US008303504B2

(12) United States Patent
Satoh

(10) Patent No.: US 8,303,504 B2
(45) Date of Patent: Nov. 6, 2012

(54) ULTRASONIC DIAGNOSTIC APPARATUS

(75) Inventor: Tomoo Satoh, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 654 days.

(21) Appl. No.: 12/195,834

(22) Filed: Aug. 21, 2008

(65) Prior Publication Data

US 2009/0054769 A1    Feb. 26, 2009

(30) Foreign Application Priority Data

Aug. 23, 2007    (JP) .................................. 2007-216962

(51) Int. Cl.
*A61B 8/00* (2006.01)
(52) U.S. Cl. ......................... 600/443; 600/407; 600/437
(58) Field of Classification Search .................. 600/407, 600/437, 441–447; 382/128
See application file for complete search history.

(56) References Cited

U.S. PATENT DOCUMENTS 5,172,343 A * 12/1992 O'Donnell ....................... 367/7
5,568,812 A * 10/1996 Murashita et al. ............ 600/440
5,622,174 A * 4/1997 Yamazaki ..................... 600/441

FOREIGN PATENT DOCUMENTS

| JP | 11-113893 A | 4/1999 |
| JP | 11-113894 A | 4/1999 |
| JP | 11-113895 A | 4/1999 |
| JP | 11-113896 A | 4/1999 |
| JP | 11-137546 A | 5/1999 |

* cited by examiner

*Primary Examiner* — Tse Chen
*Assistant Examiner* — Joel F Brutus
(74) *Attorney, Agent, or Firm* — Sughrue Mion, PLLC

(57) ABSTRACT

An ultrasonic diagnostic apparatus capable of obtaining phase information of ultrasonic waves reflected at respective sampling points within an object to be inspected and displaying the phase information in an easy-to-understand-way. The ultrasonic diagnostic apparatus includes: a transmitting and receiving unit for converting reception signals outputted from plural ultrasonic transducers, which have transmitted ultrasonic waves and received ultrasonic echoes, into digital signals; reception focus processing means for performing reception focus processing on the digital signals to generate a sound ray signal along a reception direction of ultrasonic waves; first calculating means for performing quadrature detection processing on the sound ray signal to generate a complex baseband signal; second calculating means for obtaining phase information of the complex baseband signal; and image signal generating means for generating an image signal representing phase rotation of the complex baseband signal at plural sampling points along the reception direction of ultrasonic waves based on the phase information of the complex baseband signal.

8 Claims, 8 Drawing Sheets

ULTRASONIC DIAGNOSTIC APPARATUS

BACKGROUND OF THE INVENTION

1. Field of the Invention

The present invention relates to an ultrasonic diagnostic apparatus for imaging organs within a living body and so on by transmitting and receiving ultrasonic waves to generate ultrasonic images to be used for diagnoses.

2. Description of a Related Art

In medical fields, various imaging technologies have been developed for diagnoses by observing inside of an object to be inspected. Especially, ultrasonic imaging for acquiring interior information of the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in obstetrics, but gynecology, circulatory system, digestive system, and so on.

The principle of ultrasonic imaging is as below. Ultrasonic waves are reflected at a boundary between regions with different acoustic impedances like a boundary between structures within the object. Therefore, by transmitting ultrasonic beams into the object such as a human body, receiving ultrasonic echoes generated within the object, and obtaining reflection points where the ultrasonic echoes are generated or reflection intensity, outlines of structures (e.g., internal organs, diseased tissues, and so on) existing within the object can be extracted.

The acoustic impedance is a constant intrinsic to a material as expressed by equation (1) or (2), and the unit of MRayl (mega Rayl) is generally used therefor and $1\text{Mrayl}=1\times10^6 \text{ kg}\cdot\text{m}^{-2}\cdot\text{s}^{-1}$.

$$Z=\rho\cdot C \quad (1)$$

$$Z=(\rho\cdot K)^{1/2} \quad (2)$$

where "$\rho$" represents density of an acoustic medium, "$C$" represents acoustic velocity within the acoustic medium, and "$K$" represents a bulk modulus of the acoustic medium.

Further, given that the acoustic impedance of the first medium is $Z_1$ and the acoustic impedance of the second medium adjacent to the first medium is $Z_2$, the vertical reflectance "$R$" of ultrasonic waves at the interface between the first medium and the second medium is given by the following equation (3).

$$R=(Z_2-Z_1)/(Z_2+Z_1) \quad (3)$$

Generally, an ultrasonic image is generated based on the intensity of ultrasonic waves reflected at the respective sampling points within the object, but an attempt to obtain information within the object based on phases of ultrasonic waves has been made. Especially, when $Z_1>Z_2$, the reflectance R is negative and the phases of ultrasonic waves are inverted, and therefore, the attempt is considered to be effective for acquiring tissue properties within the object.

As related technologies, Japanese Patent Application Publication JP-A-11-113893 discloses an ultrasonic diagnostic apparatus including complex signal converting means for converting a reception signal obtained by transmitting and receiving ultrasonic waves into a complex signal, and image forming means for forming an ultrasonic image based on only one of a real part and an imaginary part of the complex signal.

Japanese Patent Application Publication JP-A-11-113894 discloses an ultrasonic diagnostic apparatus including complex signal converting means for converting a reception signal obtained by transmitting and receiving ultrasonic waves into a complex signal, phase difference calculating means for calculating phases of respective sampling points on an ultrasonic beam from the complex signal to obtain phase differences between the respective sampling points by phase comparison, and variance calculating means for calculating a variance of the phase differences.

Japanese Patent Application Publication JP-A-11-113895 discloses an ultrasonic diagnostic apparatus including complex signal converting means for converting a reception signal obtained by transmitting and receiving ultrasonic waves into a complex signal, phase difference calculating means for calculating phases of the respective sampling points from the complex signal, and phase display means for displaying the phases.

Japanese Patent Application Publication JP-A-11-113896 discloses an ultrasonic diagnostic apparatus including complex signal converting means for converting a reception signal obtained by transmitting and receiving ultrasonic waves into a complex signal, ratio calculating means for calculating a ratio between a real part and an imaginary part of the complex signal, and display means for displaying the ratio between the real part and the imaginary part.

Japanese Patent Application Publication JP-A-11-137546 discloses an ultrasonic diagnostic apparatus including complex signal converting means for converting a reception signal obtained by transmitting and receiving ultrasonic waves into a complex signal, and phase difference calculating means for calculating phases of respective sampling points on an ultrasonic beam from the complex signal to obtain phase differences by phase comparison between the sampling points, wherein an ultrasonic image representing properties of living body tissues based on the phase differences is displayed.

In the above-mentioned documents, the complex signal is obtained by quadrature detection processing of the reception signal, however, the documents do not disclose display of the phase information in an easy-to-understand way based on the results. Further, the amount of information of the complex signal in the low-frequency band is small because it is sampled at a lower sampling rate than that for the original reception signal and the noise contained in the complex signal affects thereon, and accordingly, there is a problem that the phase calculation accuracy can not be obtained sufficiently.

SUMMARY OF THE INVENTION

The present invention has been achieved in view of the above-mentioned problems. A purpose of the present invention is to provide an ultrasonic diagnostic apparatus capable of obtaining phase information of ultrasonic waves reflected at the respective sampling points within the object and displaying the phase information in an easy-to-understand way. A further purpose of the present invention is to realize sufficient phase calculation accuracy for detecting inversion of phase at a boundary between different regions.

In order to accomplish the above-mentioned purposes, an ultrasonic diagnostic apparatus according to one aspect of the present invention includes: a transmitting and receiving unit for supplying drive signals to plural ultrasonic transducers to transmit ultrasonic waves and converting reception signals outputted from the plural ultrasonic transducers, which have received ultrasonic echoes, into digital signals; reception focus processing means for performing reception focus processing on the digital signals to generate a sound ray signal along a reception direction of ultrasonic waves; first calculating means for performing quadrature detection processing on the sound ray signal generated by the reception focus processing means to generate a complex baseband signal; second calculating means for obtaining phase information of the complex baseband signal; and image signal generating means for generating an image signal representing phase rotation of the complex baseband signal at plural sampling points along the reception direction of ultrasonic waves based on the phase information of the complex baseband signal.

According to the present invention, the phase information can be displayed in an easy-to-understand-way by obtaining the phase information of the complex baseband signal and generating the image signal representing phase rotation of the complex baseband signal at plural sampling points along the reception direction of ultrasonic waves. Furthermore, in the case where the complex baseband signal, or the phase information and/or amplitude information of the complex baseband signal is interpolated, sufficient phase calculation accuracy can be realized.

DESCRIPTION OF THE PREFERRED EMBODIMENTS

Hereinafter, embodiments of the present invention will be described in detail with reference to the drawings.

Figure 1:
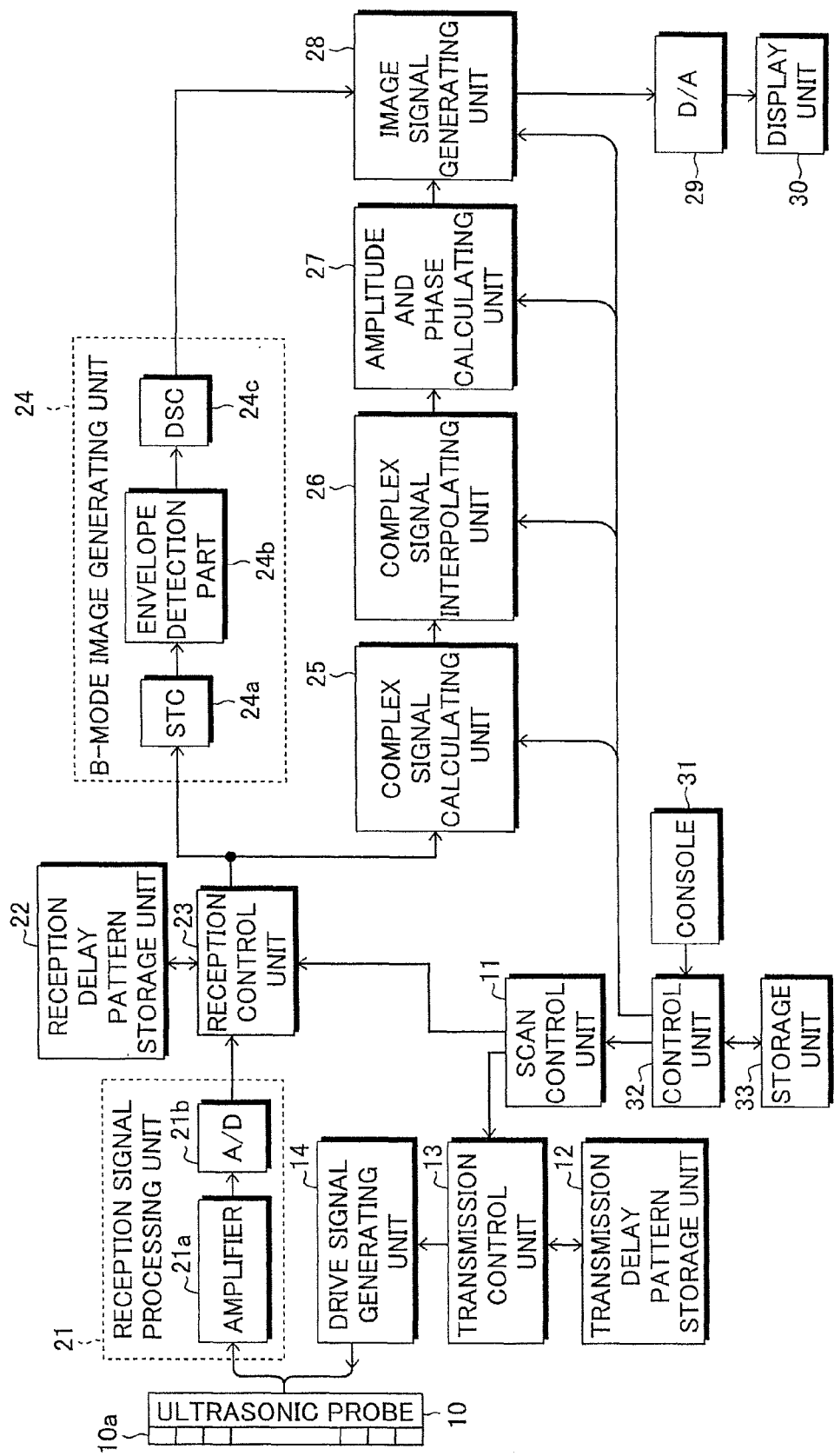
FIG. 1 is a block diagram showing a configuration of an ultrasonic diagnostic apparatus according to the first embodiment of the present invention.

FIG. 1 is a block diagram showing a configuration of an ultrasonic diagnostic apparatus according to the first embodiment of the present invention. The ultrasonic diagnostic apparatus includes an ultrasonic probe 10, a scan control unit 11, a transmission delay pattern storage unit 12, a transmission control unit 13, a drive signal generating unit 14, a reception signal processing unit 21, a reception delay pattern storage unit 22, a reception control unit 23, a B-mode image generating unit 24, a complex signal calculating unit 25, a complex signal interpolating unit 26, an amplitude and phase calculating unit 27, an image signal generating unit 28, a D/A converter 29, a display unit 30, a console 31, a control unit 32, and a storage unit 33.

The ultrasonic probe 10 is used in contact with an object to be inspected, and includes plural ultrasonic transducers 10a forming a one-dimensional or two-dimensional transducer array. These ultrasonic transducers 10a transmit an ultrasonic beam based on applied drive signals, and receive propagating ultrasonic echoes to output reception signals.

Each ultrasonic transducer includes a vibrator having electrodes formed on both ends of a material having a piezoelectric property (piezoelectric material) such as a piezoelectric ceramic represented by PZT (Pb(lead) zirconate titanate), a polymeric piezoelectric element represented by PVDF (polyvinylidene difluoride), or the like. When a pulse or continuous wave voltage is applied to the electrodes of the vibrator, the piezoelectric material expands and contracts. By the expansion and contraction, pulse or continuous wave ultrasonic waves are generated from the respective vibrators, and an ultrasonic beam is formed by synthesizing these ultrasonic waves. Further, the respective vibrators expand and contract by receiving the propagating ultrasonic waves to generate electric signals. These electric signals are outputted as reception signals of ultrasonic waves.

The scan control unit 11 sequentially sets the transmission direction of an ultrasonic beam and the reception direction of ultrasonic echoes. The transmission delay pattern storage unit 12 has stored plural transmission delay patterns to be used when the ultrasonic beam is formed. The transmission control unit 13 selects one of the plural transmission delay patterns stored in the transmission delay pattern storage unit 12 according to the transmission direction set in the scan control unit 11, and sets delay times to be provided to drive signals for the plural ultrasonic transducers 10a based on the selected transmission delay pattern.

The drive signal generating unit 14 includes plural pulsers corresponding to the plural ultrasonic transducers 10a, for example. The drive signal generating unit 14 may adjust the delay amounts of the drive signals based on the transmission delay pattern selected by the transmission control unit 13 and supply the drive signals to the ultrasonic probe 10 such that the ultrasonic waves transmitted from the plural ultrasonic transducers 10a may form an ultrasonic beam, or may supply drive signals such that the ultrasonic waves transmitted at a time from the plural ultrasonic transducers 10a may reach the entire imaging region of the object.

The reception signal processing unit 21 includes plural preamplifiers 21a and plural A/D converters 21b corresponding to the plural ultrasonic transducers 10a. The reception signals outputted from the respective ultrasonic transducers 10a are amplified in the amplifiers 21a and the analog reception signals outputted from the amplifiers 21a are converted into digital reception signals by the A/D converters 21b. The A/D converters 21b output the digital reception signals to the reception control unit 23.

The reception delay pattern storage unit 22 has stored plural reception delay patterns to be used when reception focus processing is performed on the reception signals outputted from the plural ultrasonic transducers 10a. The reception control unit 23 selects one of the plural reception delay patterns stored in the reception delay pattern storage unit 22 according to the reception direction set in the scan control unit 11, and performs reception focus processing by providing delays to the reception signals based on the selected reception delay pattern and adding the reception signals to one another. By the reception focus processing, a sound ray signal, in which the focus of the ultrasonic echoes is narrowed, is formed.

The B-mode image generating unit 24 generates a B-mode image signal as tomographic image information on tissues within the object based on the sound ray signal formed by the reception control unit 23. The B-mode image generating unit 24 includes an STC (sensitivity time control) part 24a, an envelope detection part 24b, and a DSC (Digital Scan Converter) 24c.

The STC part 24a performs correction of attenuation due to a distance on the sound ray signal formed by the reception control unit 23 according to the depths of the reflection positions of ultrasonic waves. The envelope detection part 24b performs envelope detection processing on the sound ray signal corrected by the STC part 24a to generate an envelope signal. The DSC 24c converts (raster-converts) the envelope signals generated by the envelope detection part 24b into an image signal that follows the normal scan system of television signals and performs necessary image processing such as gradation processing to generate a B-mode image signal.

The complex signal calculating unit 25 performs quadrature detection processing on the sound ray signal formed by the reception control unit 23 to generate a complex baseband signal. For explanation of the quadrature detection processing, assume that ultrasonic wave (plane wave) $\Phi$ traveling in the z-axis direction as the reception direction of ultrasonic waves is expressed by the equation (4).

$$\Phi = \Phi_0 \exp(j\omega t - kz) \tag{4}$$

where "$\Phi_0$" represents an initial value of amplitude of ultrasonic waves, "j" represents an imaginary unit, "$\omega$" represents an angular frequency of ultrasonic waves, "t" represents time, and "k" represents a variable determined depending on a tissue within the object.

What is actually measured as the sound ray signal is only the real component in the equation (4), but complex baseband signal "V" expressed by the equation (5) can be generated by performing quadrature detection processing on the measured sound ray signal.

$$V = x + jy \tag{5}$$

That is, by multiplying the ultrasonic wave "$\Phi$" by I-signal and Q-signal having substantially the same angular frequency as the angular frequency "$\omega$" of the ultrasonic wave "$\Phi$" with a 90° phase shift relative to each other, the ultrasonic wave "$\Phi$" is detected in I-phase (real number axis) and Q-phase (imaginary number axis) orthogonal to each other. Thereby, the complex baseband signal "V" has I-phase component (real component) "x" and Q-phase component (imaginary component) "y".

The complex baseband signal "V" is obtained at a predetermined number of sampling points along the reception direction of ultrasonic waves. However, for convenience of measurement, the number of sampling points is limited. On this account, the complex signal interpolating unit 26 interpolates the complex baseband signal "V" generated by the complex signal calculating unit 25, and thereby, the number of sampling points for display is made larger than the number of sampling points at measurement.

Then, the amplitude and phase calculating unit 27 obtains amplitude "A" and phase "$\theta$" of the complex baseband signal interpolated by the complex signal interpolating unit 26 according to the equations (6) and (7).

$$A = (x^2 + y^2)^{1/2} \tag{6}$$

$$\theta = \tan^{-1}(y/x) \tag{7}$$

Here, the amplitude and phase calculating unit 27 obtains the amplitude information and phase information of the complex baseband signal, however, only the phase information of the complex baseband signal may be obtained according to need.

The image signal generating unit 28 generates an image signal representing phase rotation of the complex baseband signal at the plural sampling points along the reception-direction of ultrasonic waves based on the phase information of the complex baseband signal obtained by the amplitude and phase calculating unit 27. Further, the image signal generating unit 28 may generate an image signal representing vectors of the complex baseband signal at the plural sampling points along the reception direction of ultrasonic waves based on the phase information and the amplitude information of the complex baseband signal obtained by the amplitude and phase calculating unit 27.

For example, the image signal generating unit 28 generates an image signal for display formed by synthesizing a B-mode image based on the B-mode image signal generated by the B-mode image generating unit 24 and an image representing phase rotation of the complex baseband signal at plural sampling points along a segment of line designated in the B-mode image. Thereby, the image representing the phase rotation of the complex baseband signal is synthesized with the B-mode image of the object.

The D/A converter 29 converts the digital image signal outputted from the image signal generating unit 28 into an analog image signal. The display unit 30 includes a display device such as a CRT, LCD, or the like, and displays diagnostic images based on the analog image signal.

The control unit 32 controls the scan control unit 11 and the complex signal calculating unit 25 to image signal generating unit 28 according to the operation of an operator using the console 31. The above-mentioned scan control unit 11, transmission control unit 13, reception control unit 23, B-mode image generating unit 24 to image signal generating unit 28, and control unit 32 can be realized by a CPU and software (programs). The software (programs) is stored in the storage unit 33. As a recording medium in the storage unit 33, not only a built-in hard disk but also a flexible disk, MO, MT, RAM, CD-ROM, DVD-ROM, or the like may be used.

Figure 2:
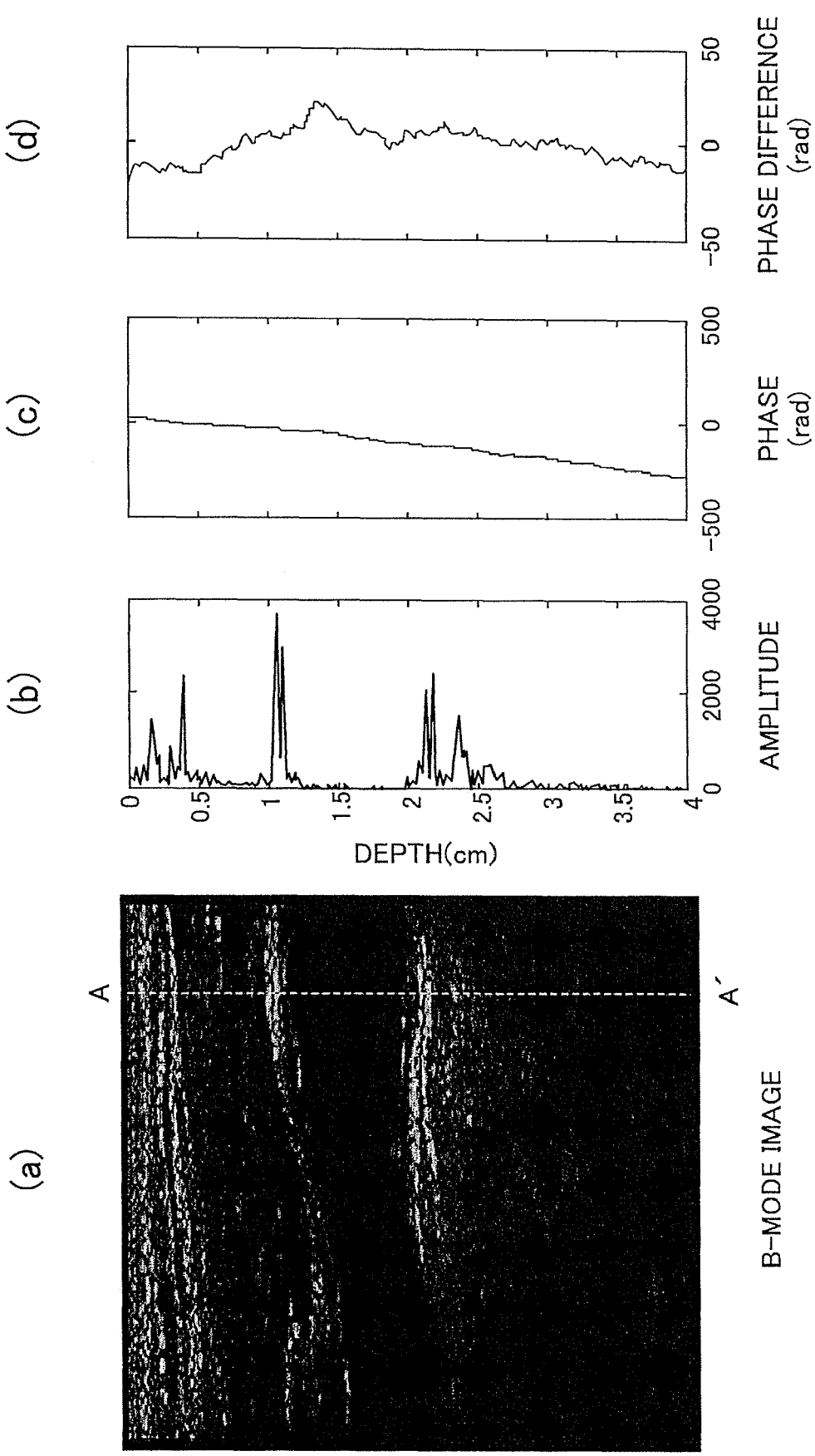
FIG. 2 shows a first example of a diagnostic image displayed on a display unit.

FIG. 2 shows a first example of a diagnostic image displayed on the display unit. This diagnostic image is obtained by imaging a carotid artery of an object to be inspected. The diagnostic image shown in FIG. 2 includes a (a) B-mode image of the object, (b) an image representing amplitudes of a complex baseband signal, (c) an image representing phases of the complex baseband signal, and (d) an image representing phase differences (amounts of phase rotation) relative to the linear approximation of the phase of the complex baseband signal. In FIG. 2, the vertical axis indicates the depth within the object.

First, (a) the B-mode image is displayed on the display unit 30 shown in FIG. 1. When an operator uses the console 31 to designate a vertical line (broken line A-A' in the image) representing the reception direction of ultrasonic waves, under the control of the control unit 32, the complex signal calculating unit 25 obtains a complex baseband signal at plural sampling points along the designated vertical line. Then, the complex signal interpolating unit 26 interpolates the complex baseband signal, and the amplitude and phase calculating unit 27 obtains amplitudes, phases, and amounts of phase rotation of the interpolated complex baseband signal. The image signal generating unit 28 generates an image signal for displaying the amplitudes, phases, and amounts of phase rotation of the complex baseband signal, and the amplitudes, phases, and amounts of phase rotation of the complex baseband signal as well as the B-mode image are displayed on the display unit 30. In this manner, it becomes easier to acquire the amounts of phase rotation of the complex baseband signal by displaying the amounts of phase rotation of the complex baseband signal.

Figure 3:
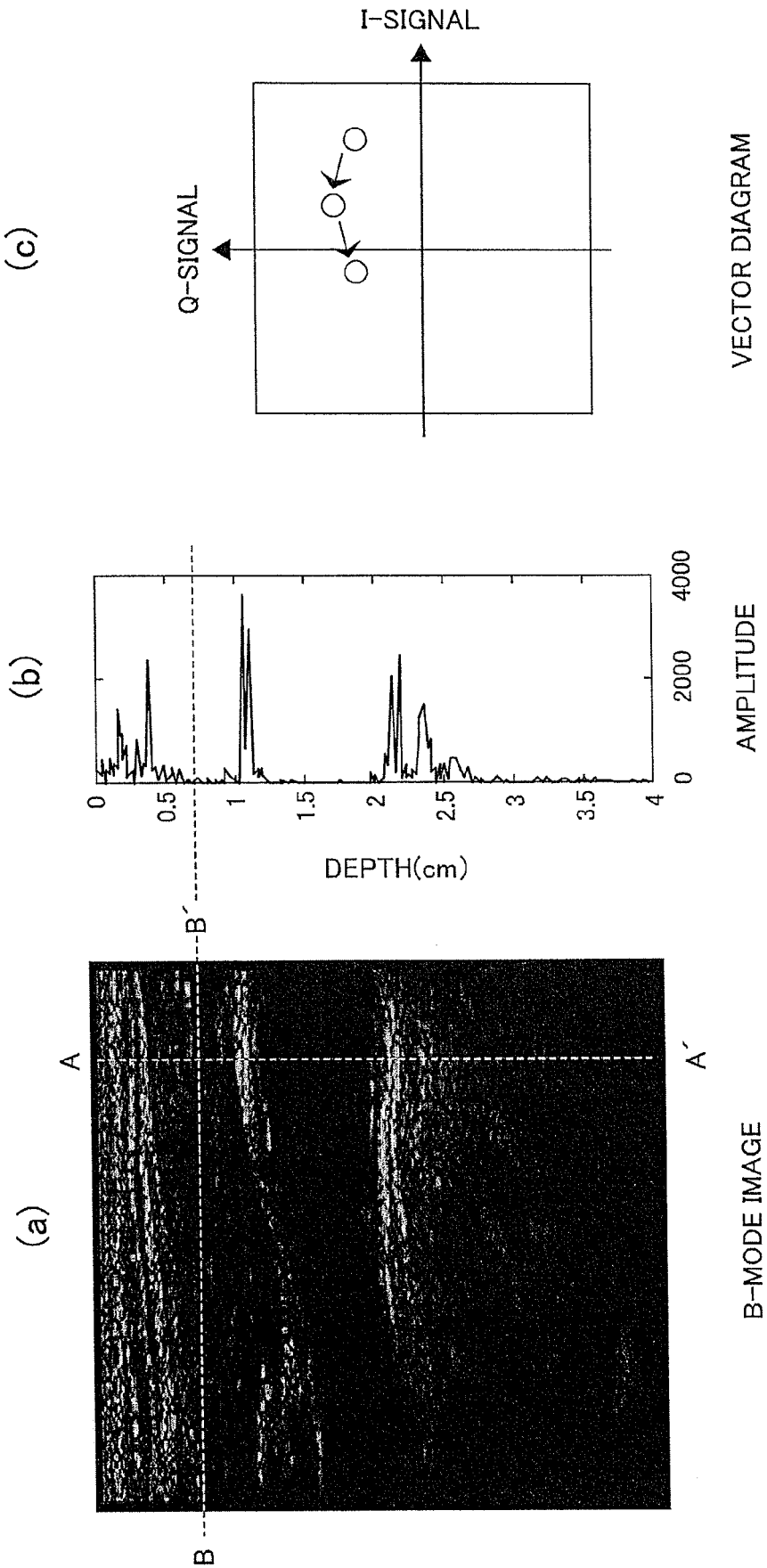
FIG. 3 shows a second example of a diagnostic image displayed on the display unit.

FIG. 3 shows a second example of a diagnostic image displayed on the display unit. This diagnostic image is obtained by imaging a carotid artery of an object to be inspected. The diagnostic image shown in FIG. 3 includes (a) a B-mode image of the object, (b) an image representing amplitudes of a complex baseband signal, and (c) a vector diagram of the complex baseband signal. In FIG. 3, the vertical axis indicates the depth within the object.

First, (a) the B-mode image is displayed on the display unit 30 shown in FIG. 1. When an operator uses the console 31 to designate a vertical line (broken line A-A' in the image) representing the reception direction of ultrasonic waves, under the control of the control unit 32, the complex signal calculating unit 25 obtains a complex baseband signal at plural sampling points along the designated vertical line. Then, the complex signal interpolating unit 26 interpolates the complex baseband signal, and the amplitude and phase calculating unit 27 obtains amplitudes and phases of the interpolated complex baseband signal. The image signal generating unit 28 generates an image signal for displaying the amplitudes of the complex baseband signal, and the amplitudes of the complex baseband signal as well as the B-mode image are displayed on the display unit 30.

Furthermore, when the operator uses a mouse or the like to click a start button, the horizontal line (the broken line B-B' in the image) moves from the upper end to the lower end in (a) the B-mode image, and the image signal generating unit 28 generates an image signal for displaying leading end positions of vectors of the complex baseband signal corresponding to intersection points of the vertical line and the horizontal line, and the leading end positions of the vectors of the complex baseband signal are cumulatively displayed in (c) the vector diagram. In this manner, it becomes easier to acquire the movement of phase rotation of the complex baseband signal by displaying the vectors of the complex baseband signal as moving images.

Next, the second embodiment of the present invention will be explained.

Figure 4:
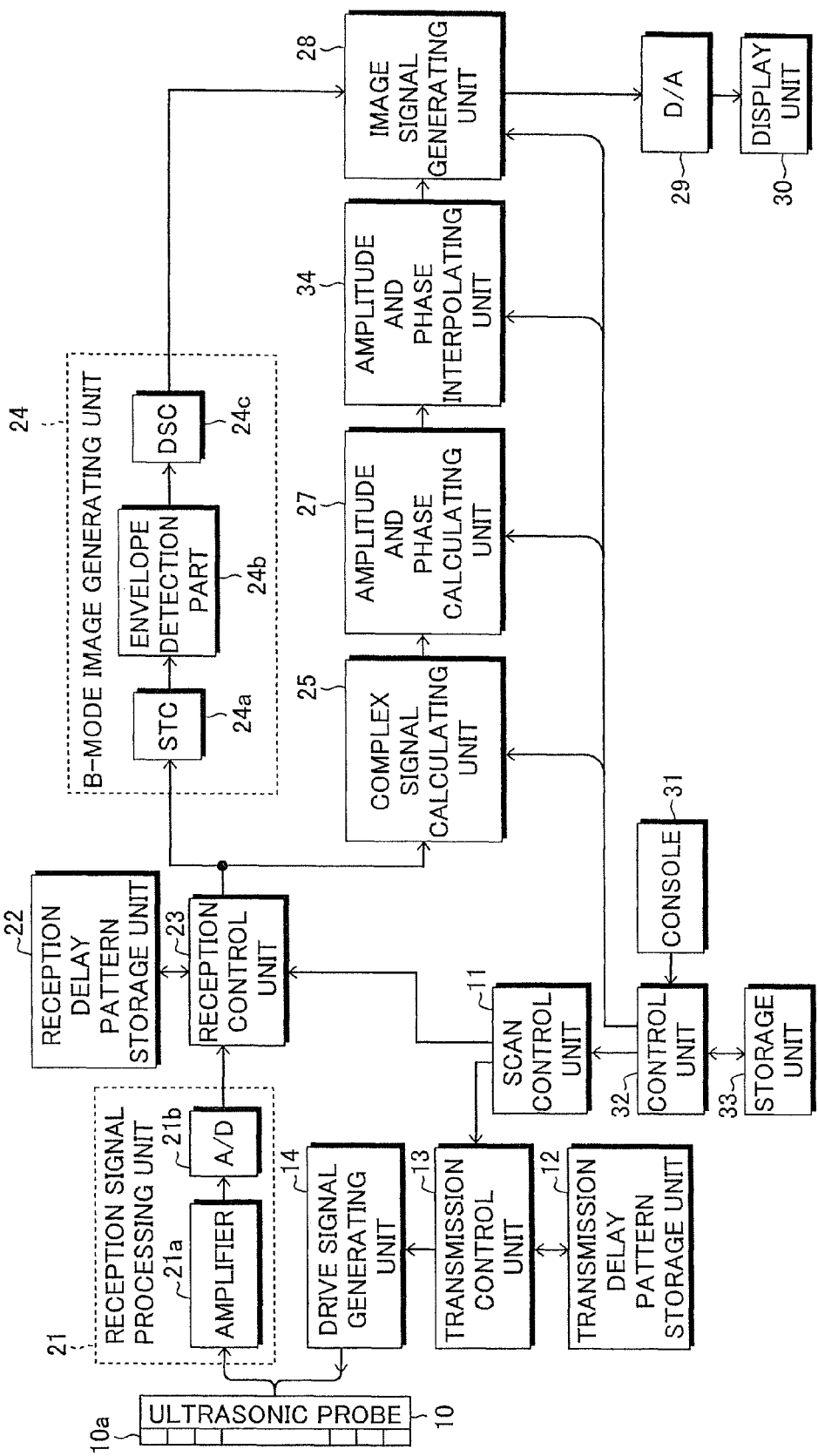
FIG. 4 is a block diagram showing a configuration of an ultrasonic diagnostic apparatus according to the second embodiment of the present invention.

FIG. 4 is a block diagram showing a configuration of an ultrasonic diagnostic apparatus according to the second embodiment of the present invention. An ultrasonic diagnostic apparatus according to the second embodiment is provided with an amplitude and phase interpolating unit 34 in place of the complex signal interpolating unit 26 in the first embodiment shown in FIG. 1, and the rest of the configuration is the same as that of the first embodiment.

The complex signal calculating unit 25 generates a complex baseband signal "V" expressed by the equation (5) by performing quadrature detection processing on the sound ray signal formed by the reception control unit 23.

$$V = x + jy \quad (5)$$

Then, the amplitude and phase calculating unit 27 obtains amplitude "A" and phase "θ" of the complex baseband signal generated by the complex signal calculating unit 25 according to the equations (6) and (7).

$$A = (x^2 + y^2)^{1/2} \quad (6)$$

$$\theta = \tan^{-1}(y/x) \quad (7)$$

Here, the amplitude and phase calculating unit 27 obtains the amplitude information and phase information of the complex baseband signal, however, only the phase information of the complex baseband signal may be obtained according to use.

The amplitudes "A" and phases "θ" of the complex baseband signal are obtained at a predetermined number of sampling points along the reception direction of ultrasonic waves. However, for convenience of measurement, the number of sampling points is limited. On this account, the amplitude and phase interpolating unit 34 interpolates the amplitudes "A" and phases "θ" obtained by the amplitude and phase calculating unit 27, and thereby, the number of sampling points is increased.

The image signal generating unit 28 generates an image signal representing phase rotation of the complex baseband signal at the plural sampling points along the reception direction of ultrasonic waves based on the phase information of the complex baseband signal interpolated by the amplitude and phase interpolating unit 34. Furthermore, the image signal generating unit 28 may generate an image signal representing vectors of the complex baseband signal at the plural sampling points along the reception direction of ultrasonic waves based on the phase information and the amplitude information interpolated by the amplitude and phase interpolating unit 34.

Figure 5:
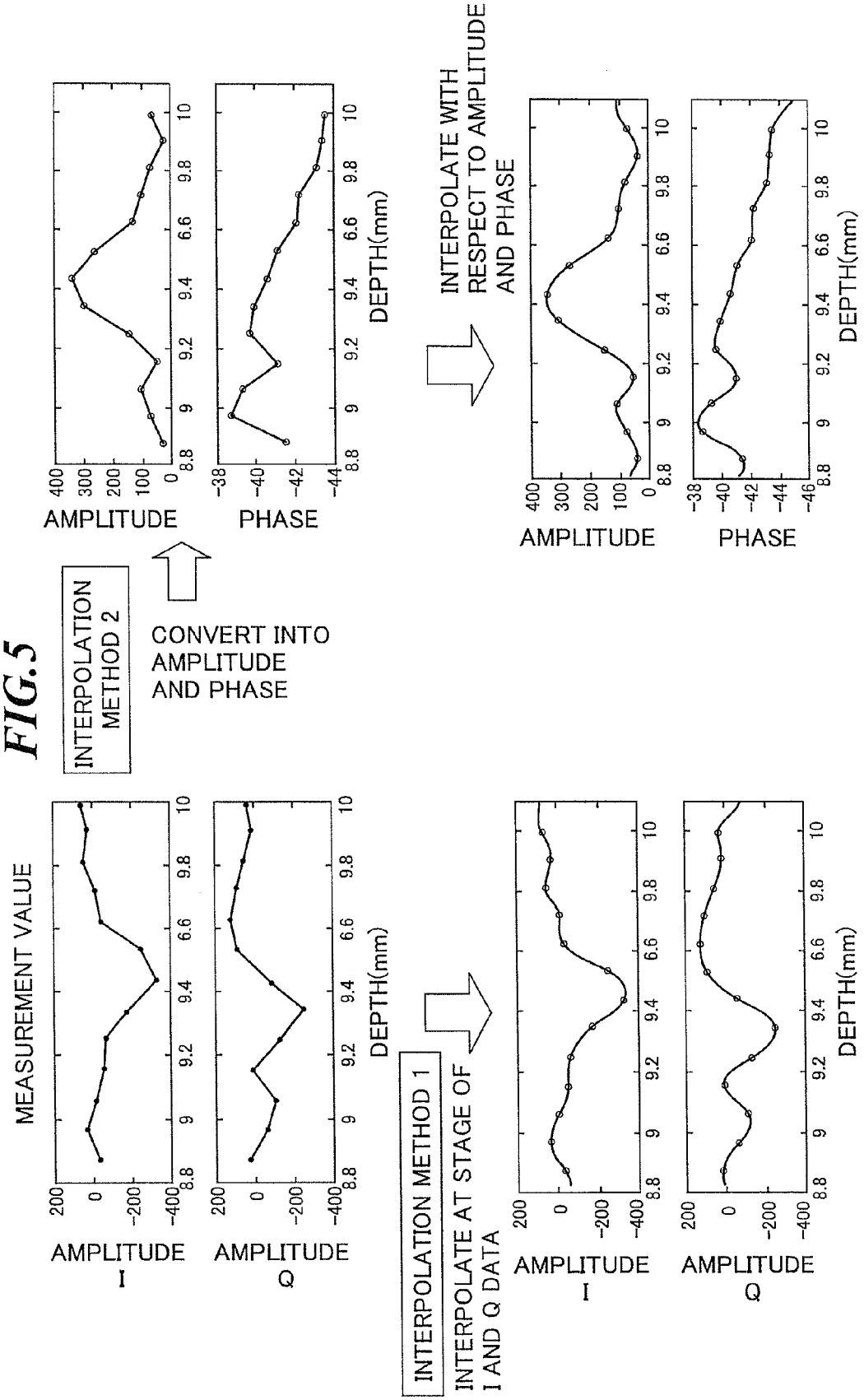
FIG. 5 is a diagram for explanation of the difference between the interpolation methods in the first embodiment and the second embodiment.

Next, the difference between the interpolation methods in the above explained first embodiment and second embodiment will be explained. FIG. 5 is a diagram for explanation of the difference between the interpolation methods in the first embodiment and the second embodiment. The complex baseband signal has an I-phase component and a Q-phase component (also referred to as "IQ data" as below). In FIG. 5, the horizontal axis indicates the depth within the object and the vertical axis indicates amplitude "I" of the I-phase component or amplitude "Q" of the Q-phase component.

As shown in FIG. 5, according to the interpolation method 1 in the first embodiment, the measurement values of the complex baseband signal are interpolated in the stage of IQ data. On the other hand, according to the interpolation method 2 in the second embodiment, the measurement values of the complex baseband signal are converted into amplitudes and phases, and the amplitudes and phases are interpolated. In either case, because of the interpolation, the polygonal line showing changes in amplitude or phase depending on the depth becomes smoother and the image accuracy to be displayed is improved.

Figure 6:
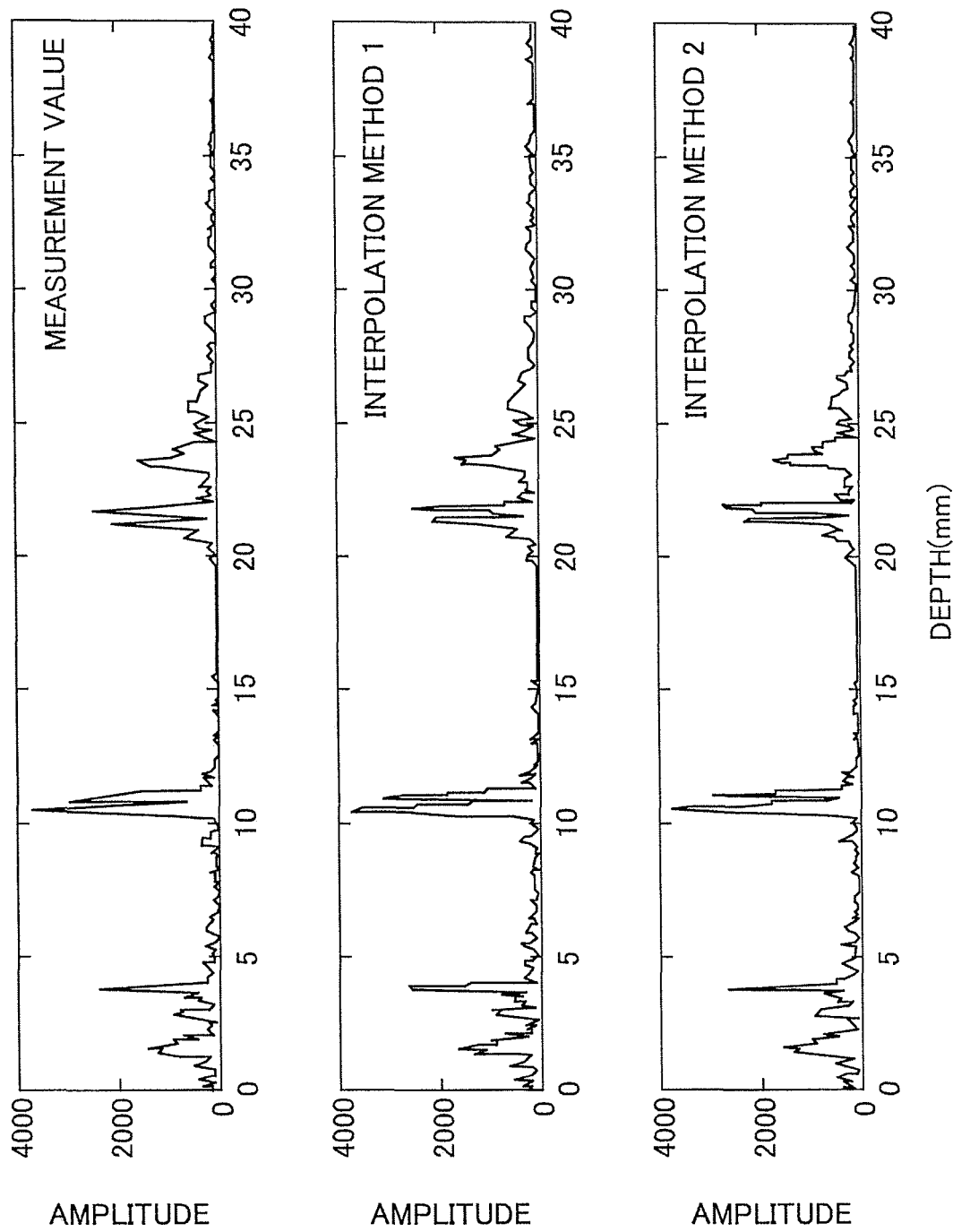
FIG. 6 is a diagram for comparison between the amplitudes of the complex baseband signal obtained by the interpolation methods in the first embodiment and the second embodiment.

FIG. 6 is a diagram for comparison between the amplitudes of the complex baseband signal obtained by the interpolation methods in the first embodiment and the second embodiment. FIG. 6 shows the measurement values of the amplitude of the complex baseband signal, the amplitude obtained based on the IQ data interpolated according to the interpolation method 1 and the amplitude interpolated according to the interpolation method 2. As shown in FIG. 6, there is not so much of difference between the amplitudes depending on the interpolation methods.

Figure 7:
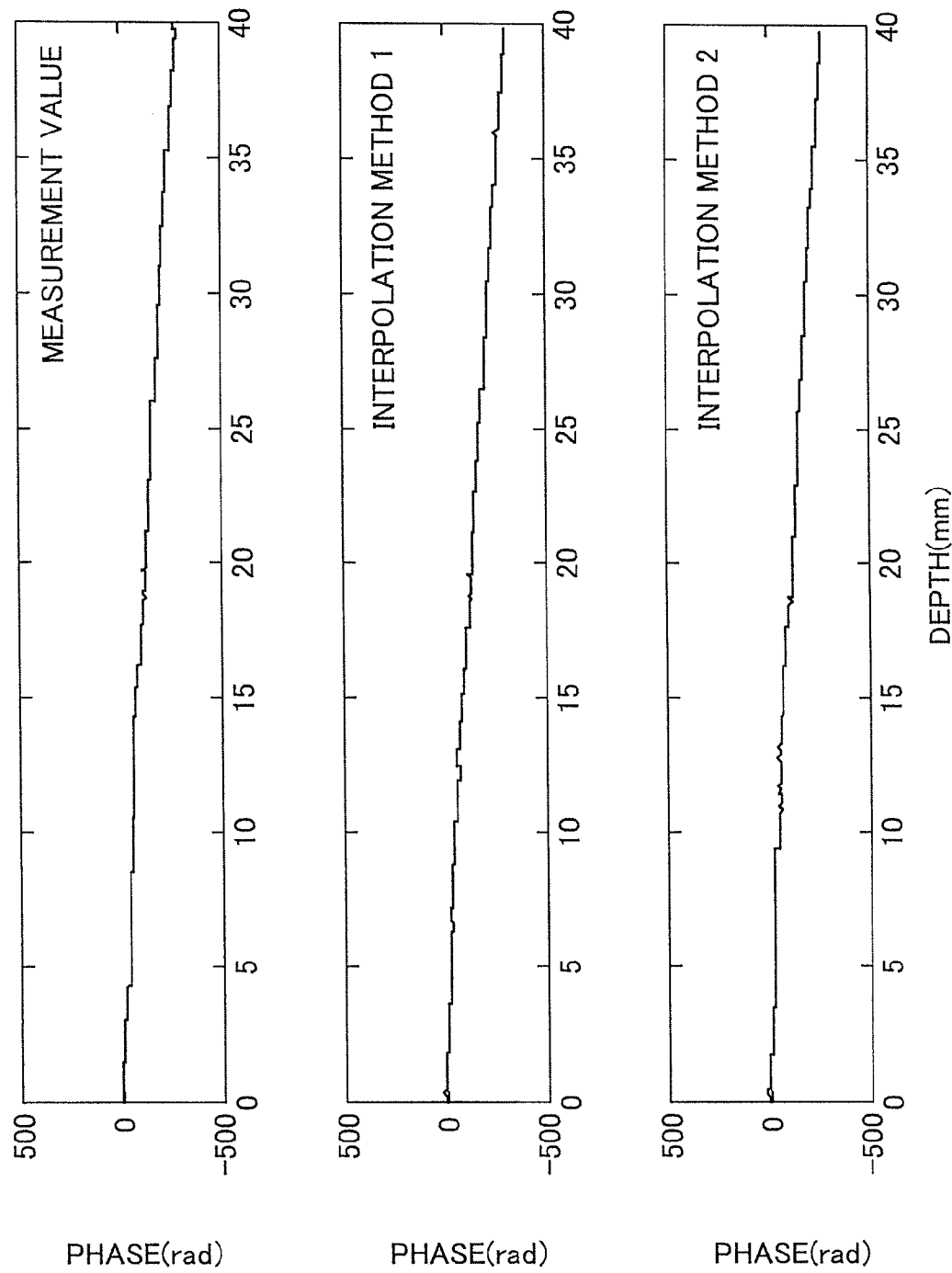
FIG. 7 is a diagram for comparison between the phases of the complex baseband signal obtained by the interpolation methods in the first embodiment and the second embodiment.

FIG. 7 is a diagram for comparison between the phase of the complex baseband signal obtained by the interpolation methods in the first embodiment and the second embodiment. FIG. 7 shows the measurement values of the phase of the complex baseband signal, the phase obtained based on the IQ data interpolated according to the interpolation method 1 and the phase interpolated according to the interpolation method 2. As shown in FIG. 7, there is a difference between the phases depending on the interpolation methods.

Figure 8:
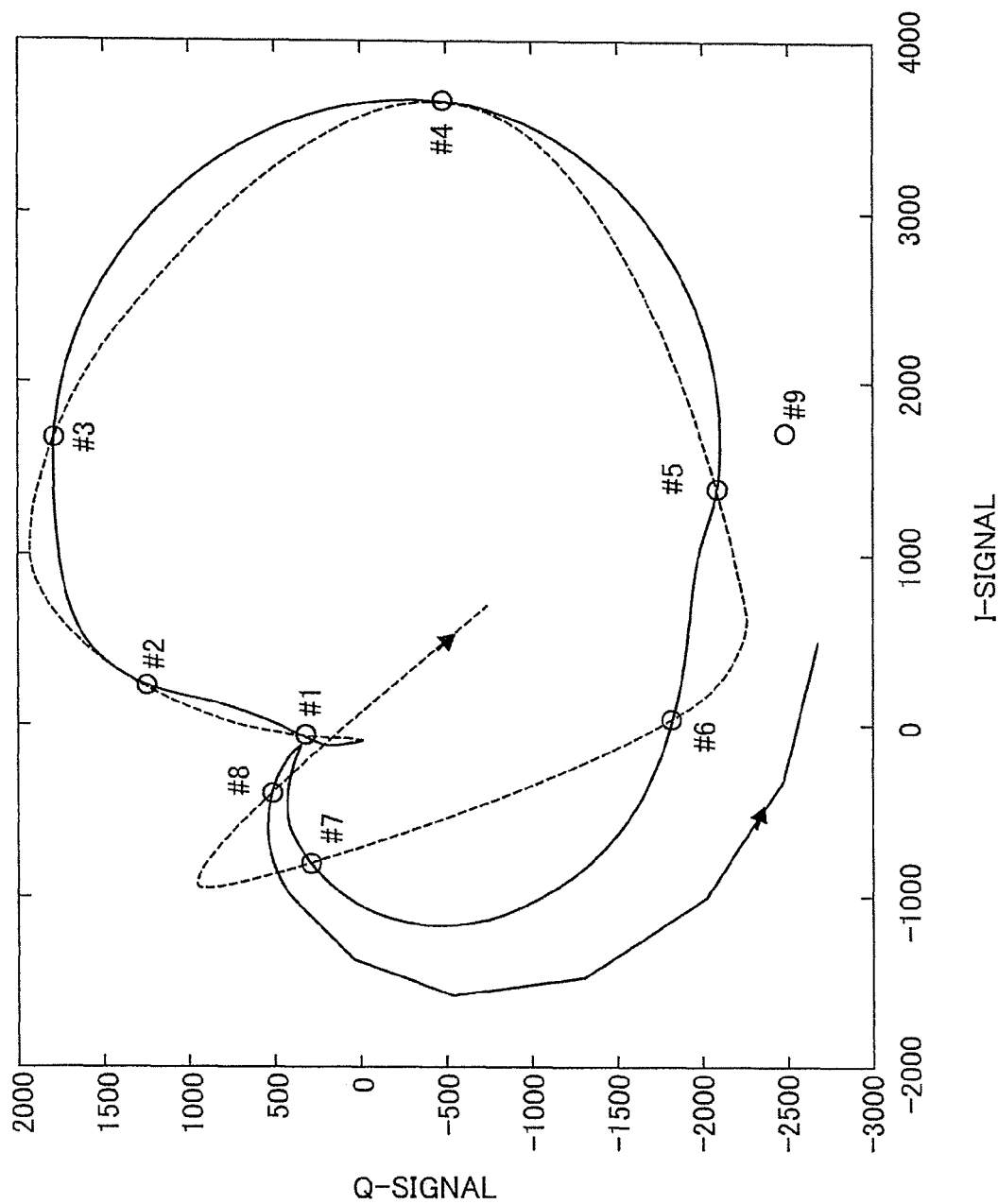
FIG. 8 is a diagram for comparison between the vectors of the complex baseband signal obtained by the interpolation methods in the first embodiment and the second embodiment.

FIG. 8 is a diagram for comparison between the vectors of the complex baseband signals obtained by the interpolation methods in the first embodiment and the second embodiment. Here, the horizontal axis indicates the amplitude of I-signal and the vertical axis indicates the amplitude of Q-signal. In FIG. 8, the measurement values (circles) of the vectors of the complex baseband signal at nine sampling points #1 to #9 and the vector locus (broken line) having the amplitudes and phases obtained based on the IQ data interpolated according to the interpolation method 1 and the vector locus (solid line) having the amplitudes and phases interpolated according to the interpolation method 2. As shown in FIG. 8, there is a large difference between the rotational directions of the vectors, i.e., the amounts of phase rotation from the sampling point #8 to the sampling point #9 depending on the interpolation methods. According to the interpolation method 2, there is shown the condition that the vector rotation changes from the clockwise rotation to the counter-clockwise rotation, and the occurrence of phase inversion can be clearly observed.

The invention claimed is:

1. An ultrasonic diagnostic apparatus comprising:
    a transmitting and receiving unit for supplying drive signals to plural ultrasonic transducers to transmit ultrasonic waves and converting reception signals outputted from said plural ultrasonic transducers, which have received ultrasonic echoes, into digital signals;
    a reception focus processing unit for performing reception focus processing on the digital signals to generate a sound ray signal along a reception direction of ultrasonic waves;
    a B-mode image generating unit for generating a B-mode image signal representing a B-mode image based on the sound ray signal generated by said reception focus processing unit;
    a console to be used for designating a line in the B-mode image;
    a first calculating unit for performing quadrature detection processing on the sound ray signal generated by said reception focus processing unit to generate a complex baseband signal at plural sampling points along the designated line;
    a second calculating unit for obtaining phase information of the complex baseband signal;
    an image signal generating unit for generating an image signal representing an image of phase differences of the complex baseband signal at the plural sampling points along the designated line relative to a linear approximation of a phase of the complex baseband signal based on the phase information of the complex baseband signal; and
    a display unit for displaying the B-mode image together with the image of the phase differences of the complex baseband signal.

2. The ultrasonic diagnostic apparatus according to claim 1, wherein:
    said second calculating unit further obtains amplitude information of the complex baseband signal;
    said image signal generating unit generates an image signal representing an image of leading end positions of vectors of the complex baseband signal at the plural sampling points along the designated line based on the phase information and the amplitude information of the complex baseband signal; and
    said display unit displays the B-mode image together with the image of the leading end positions of the vectors of the complex baseband signal.

3. The ultrasonic diagnostic apparatus according to claim 2, wherein said image signal generating unit generates an image signal formed by synthesizing the B-mode image and the image of the leading end positions of the vectors of the complex baseband signal at the plural sampling points along the designated line.

4. The ultrasonic diagnostic apparatus according to claim 2, further comprising:
    a third calculating unit for interpolating the complex baseband signal generated by said first calculating unit;
    wherein said second calculating unit obtains the phase information and amplitude information of the complex baseband signal interpolated by said third calculating unit.

5. The ultrasonic diagnostic apparatus according to claim 2, further comprising:
    a third calculating unit for interpolating the phase information and amplitude information obtained by said second calculating unit;
    wherein said image signal generating unit generates the image signal representing the image of the phase rotation of the complex baseband signal based on the phase information and amplitude information interpolated by said third calculating unit.

6. The ultrasonic diagnostic apparatus according to claim 1, wherein said image signal generating unit generates an image signal formed by synthesizing the B-mode image and the image of the phase differences of the complex baseband signal at the plural sampling points along the designated line.

7. The ultrasonic diagnostic apparatus according to claim 1, further comprising:
    a third calculating unit for interpolating the complex baseband signal generated by said first calculating unit;
    wherein said second calculating means unit obtains the phase information and/or amplitude information of the complex baseband signal interpolated by said third calculating means unit.

8. The ultrasonic diagnostic apparatus according to claim 1, further comprising:
    a third calculating unit for interpolating the phase information obtained by said second calculating unit;
    wherein said image signal generating unit generates the image signal representing the image of the phase differences of the complex baseband signal based on the phase information interpolated by said third calculating unit.

* * * * *